(12) United States Patent
Topgaard

(10) Patent No.: US 8,810,244 B2
(45) Date of Patent: Aug. 19, 2014

(54) METHOD AND SYSTEM FOR MAGNETIC RESONANCE IMAGING, AND USE THEREOF

(75) Inventor: Daniel Topgaard, Lund (SE)

(73) Assignee: CR Development AB, Lund (SE)

( * ) Notice: Subject to any disclaimer, the term of this patent is extended or adjusted under 35 U.S.C. 154(b) by 389 days.

(21) Appl. No.: 13/321,332

(22) PCT Filed: Apr. 22, 2010

(86) PCT No.: PCT/SE2010/050448
§ 371 (c)(1),
(2), (4) Date: Nov. 18, 2011

(87) PCT Pub. No.: WO2010/134870
PCT Pub. Date: Nov. 25, 2010

(65) Prior Publication Data
US 2012/0062229 A1    Mar. 15, 2012

Related U.S. Application Data

(60) Provisional application No. 61/180,752, filed on May 22, 2009.

(30) Foreign Application Priority Data

May 22, 2009 (SE) ...................................... 0950363

(51) Int. Cl.
*G01V 3/00* (2006.01)
(52) U.S. Cl.
USPC .......................................................... 324/309
(58) Field of Classification Search
USPC ........................... 324/300–322; 600/410–435
See application file for complete search history.

(56) References Cited

U.S. PATENT DOCUMENTS

| 8,565,854 B2 * | 10/2013 | Bryskhe et al. ............... 600/410 |
| 2007/0238969 A1 | 10/2007 | Song et al. |

(Continued)

FOREIGN PATENT DOCUMENTS

| CN | 1636508 | 7/2005 |
| CN | 101077301 | 11/2007 |
| EP | 1550881 | 7/2005 |

(Continued)

OTHER PUBLICATIONS

International Preliminary Report on Patentability dated Nov. 22, 2011 issued on corresponding International Application No. PCT/SE2010/050448.

(Continued)

*Primary Examiner* — Dixomara Vargas
(74) *Attorney, Agent, or Firm* — Harness, Dickey & Pierce, P.L.C.

(57) ABSTRACT

The present invention refers to a method for magnetic resonance imaging or nuclear magnetic resonance spectroscopy comprising emitting a radio frequency and gradient pulse sequence towards an object being subjected to a magnetic field, wherein said object comprises a molecule having an atom with a nuclear spin differing from 0, encoding, detecting and acquiring a magnetic resonance signal from said object corresponding to said emitted radio frequency and gradient pulse sequence, wherein the radio frequency and gradient pulse sequence comprises a first weighting block, a mixing block with duration $t_m$ and a second weighting block, and wherein encoding, detecting and acquiring the magnetic resonance signal from said object is limited to initial decay of the signal intensity I with increasing strength of at least one of the first weighting block and the second weighting block, wherein the variation of the initial signal decay rate with $t_m$ is analysed to obtain the apparent exchange rate AXR.

18 Claims, 2 Drawing Sheets

(56) References Cited

U.S. PATENT DOCUMENTS

2008/0069417 A1     3/2008    Kimura
2010/0152567 A1*   6/2010    Bryskhe et al. ............... 600/410

FOREIGN PATENT DOCUMENTS

EP            1860453       11/2007
WO    WO-2008147326 A1   12/2008
WO    WO-2008147923 A1   12/2008

OTHER PUBLICATIONS

Jorg Karger et al., "Principles and application of Self-Diffusion Measurements by Nuclear Magnetic Resonance", *Adv. Magn. Reson.*, 12:1-89 (1988).

P.T. Callaghan et al., "Diffusion-diffusion correlation and exchange as a signature for local order and dynamics", *J. Chem. Phys.*, 120, pp. 4032-4038 (2004).

K.E. Washburn et al., "Tacking pore to pore exchange using relaxation exchange spectroscopy", *Phys. Rev. Lett.*, 97, 175502 (2006).

International Search Report for International Application No. PCT/SE2010/050448 filed Apr. 22, 2010.

Chinese Search Report dated Jul. 9, 2013 issued in corresponding Chinese Appln. No. 201080021664.6.

Topgaard, D. et al. "Molecular exchange in breast cells studied with a new DW-MRI method." *Proceedings of the International Society of Magnetic Resonance in Medicine* 17 (2009).

\* cited by examiner

METHOD AND SYSTEM FOR MAGNETIC RESONANCE IMAGING, AND USE THEREOF

FIELD OF THE INVENTION

This invention pertains in general to the field of Nuclear Magnetic Resonance and Magnetic Resonance Imaging.

BACKGROUND OF THE INVENTION

Diffusion Nuclear Magnetic Resonance (NMR) has been used for over 40 years to determine self-diffusion coefficients, which may be interpreted in terms of aggregate size, permeability of the medium through which the molecules are moving, and binding events occurring between the diffusing species and larger molecules or the porous matrix. The most common diffusion NMR techniques rely on a diffusion encoding block comprising pairs of magnetic field gradient pulses to label the NMR radio frequency signal for displacements occurring during the time between the pulses. Diffusion NMR techniques and methods of analysis are not only applied in vitro but also in the context of medical magnetic resonance imaging (MRI) for the detection of pathological conditions such as ischemic stroke, demyelinization disorder, and tumours. In some cases, especially for stroke, image contrast based on diffusion is more informative than the more classical modes of contrast based on the nuclear relaxation rates $R_1$ and $R_2$.

The rate of water exchange between compartments with different relaxation/diffusion characteristics is a potential useful marker for pathological conditions in tissue. Diffusion NMR experiments performed as a function of the diffusion can be analyzed with the Kärger model to estimate the rate of exchange (Kärger, J., H. Pfeifer, and W. Heink. 1988. Principles and applications of self-diffusion measurements by nuclear magnetic resonance. Adv. Magn. Reson. 12:1-89). The analysis is hampered by the weak dependence of the NMR signal on the exchange rate.

The publications P. T. Callaghan, and I. Furó, Diffusion-diffusion correlation and exchange as a signature for local order and dynamics. J. Chem. Phys. 120 (2004) 4032-4038 and K. E. Washburn, and P. T. Callaghan, Tracking pore to pore exchange using relaxation exchange spectroscopy. Phys. Rev. Lett 97 (2006) 175502. discloses two-dimensional nuclear magnetic resonance experiments for the examination of exchange processes. The methods, known as diffusion exchange spectroscopy and relaxation exchange spectroscopy, employ two independently incremented relaxation/diffusion weighting blocks separated by a mixing time, and signal analysis using two-dimensional inverse Laplace transformation. However, a serious drawback is the inordinate demands on instrument time for acquiring the large amount of data required for the two-dimensional inverse Laplace analysis, thus making the method impractical for studies of human subjects with limited patience.

In summary, up until now the currently available diffusion NMR methods for estimating exchange rates are either very time consuming (Callaghan) or rely on curve-fitting with only weak dependence between the estimated parameters and the information in the experimental data (Kärger). Other known methods that could be used to obtain the exchange times are invasive methods, such as observations of the diffusion of a marker molecule by means of light scattering, microscopy, absorption spectroscopy and X-ray. This is not only difficult to use in vivo due to the toxicology risks but one could never assure that the tissue and body fluids are unaffected by the introduced marker.

However, the PCT application WO2008/147326 discloses a method which solves the problems disclosed above. The method according to the PCT application WO2008/147326 comprises emitting a radio frequency pulse sequence towards an object being subjected to a magnetic field, wherein said object comprises a molecule having an atom with a nuclear spin differing from 0, emitting a gradient pulse sequence towards said object, detecting a magnetic resonance signal from said object corresponding to said emitted radio frequency pulse sequence, and processing said magnetic resonance signal.

Moreover, the method according to the PCT application WO2008/147326 is characterized in that said gradient pulse sequence comprises a filter block (first diffusion weighting block) configured to reduce at least a part of the distribution of diffusion coefficients of said object, and a diffusion encoding block (a second diffusion weighting block) occurring at a predetermined time after emitting said filter block, and said processing comprising comparing a portion of said magnetic resonance signal with a portion of a predetermined magnetic resonance signal, resulting in a compared signal, wherein the portion of said predetermined magnetic resonance signal is either user defined or resulting from a previously applied gradient pulse sequence.

The method according to the PCT application WO2008/147326 has several advantages. The general solution according to invention of the PCT application WO2008/147326 is that it utilizes a sequence of gradient pulses as a filter on a diffusion experiment. Thereby identical molecules can be analyzed separately and differentiated based on how restricted their diffusion is. The rate of exchange between various compartments is an important parameter that is obtainable utilizing the present invention according to some specific embodiments. Moreover, the invention according to the PCT application WO2008/147326 offers a new contrast mode for MRI studies of materials, such as tissue, where the exchange rate varies as a function of position.

Furthermore, other advantages with the invention according to the PCT application WO2008/147326 are shortened overall experiment time duration needed, which as such enables the invention to be used in vivo, e.g. such as a means for contrast in Magnetic Resonance Imaging (MRI), in some cases the non-existing need for background information from other experiments, such as the shape or diffusion coefficient of the studied molecule, in order to obtain a reliable exchange rate result, and the possibility of giving an image where the contrast is dependent on differences in exchange rate.

However, there also exist problems with the method and the protocols disclosed in the PCT application WO2008/147326 and with Callaghan's protocol.

One such problem is the fact that these protocols are not applicable on all MRI instruments. Some of the standard MRI scanners used today cannot acquire enough data to allow for e.g. a method according to WO2008/147326 to be applied, such as for a global two component fit or ILT analysis.

Another problem with clinical MRI is the in general high noise levels. Due to the large data acquisition according to WO2008/147326, noise may in fact be a large problem.

One object of the present invention is to provide a method for MRI, which method is applicable to a very wide range of MRI scanners, such as the standard clinical whole-body MRI scanners used today. Another object of the present invention is to provide a method for MRI which is not largely affected by noise.

SUMMARY OF THE INVENTION

The objects disclosed above are solved by a method for magnetic resonance imaging or nuclear magnetic resonance spectroscopy comprising emitting a radio frequency and gradient pulse sequence towards an object being subjected to a magnetic field, wherein said object comprises a molecule having an atom with a nuclear spin differing from 0;
encoding, detecting and acquiring a magnetic resonance signal from said object corresponding to said emitted radio frequency and gradient pulse sequence, wherein the radio frequency and gradient pulse sequence comprises a first weighting block, a mixing block with duration $t_m$ and a second weighting block; wherein
encoding, detecting and acquiring the magnetic resonance signal from said object is limited to initial decay of the signal intensity I with increasing strength of at least one of the first weighting block and the second weighting block, wherein the variation of the initial signal decay rate with $t_m$ is analysed to obtain the apparent exchange rate AXR.

In comparison to previous protocol described in WO2008/147326, less signal attenuation is needed to get the information about exchange. For the case of diffusion weighting, less signal attenuation means that correspondingly lower values of the diffusion weighting parameter b and the gradient amplitude G can be used. The protocol can thus be implemented on any clinical MRI scanner and not only the most modern ones with very high maximum gradient strength (>40 mT/m). Less signal attenuation also means that the signal is less affected by noise.

GENERAL FOUNDATION OF THE PRESENT INVENTION

The general foundation of the present invention is disclosed in the PCT application WO2008/147326, which application hereby is incorporated in its entirety by reference.

Figure 1:
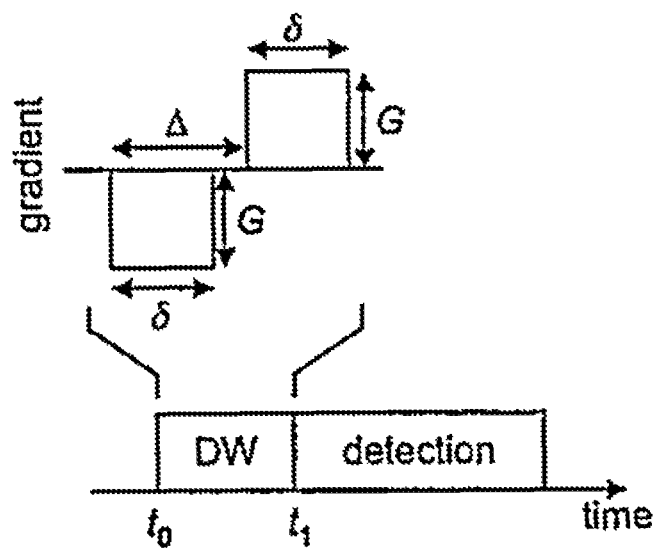
FIG. 1 shows the commonly known general pulse sequence for diffusion weighted nuclear magnetic resonance (NMR) or magnetic resonance imaging (MRI).

Below, this general foundation will be described shortly.
Diffusion Weighted NMR and MRI The commonly known general pulse sequence for diffusion weighted nuclear magnetic resonance (NMR) or magnetic resonance imaging (MRI) is shown in FIG. 1. A diffusion weighting (DW) block is inserted before the detection block, thereby inducing a molecular motion dependent attenuation of the intensity in each frequency channel for NMR, or for each pixel in MRI. The DW block in general consists of a pair of gradient pulses, most commonly being rectangular, trapezoidal, or sinusoidal in shape, separated by a refocusing 180° radiofrequency (RF) pulse inverting the phase shift induced by the previously applied gradient pulses. The first and second gradient pulse are denoted the defocusing and refocusing pulse, respectively. The simplest effective gradient shape is shown in the expansion in FIG. 1. The detection block for NMR usually involves recording the time domain signal during free precession, which after Fourier transform (FT) yields an NMR spectrum. For MRI applications, the detection block consists of a single or a series of gradient or RF echoes, which upon FT yields 1D, 2D, or 3D images. Common detection schemes include, but are not limited to, echo planar imaging, fast spin echoes, spiral imaging, propeller imaging, etc.

The signal attenuation of the DW block is commonly reported using the diffusion sensitizing variable b and the self-diffusion coefficient D by $$I = I_0 e^{-bD} \qquad (1)$$

where I is the detected signal intensity and $I_0$ is the signal intensity at zero gradient strength. The b-value is calculated by $$b = \gamma^2 \int_{t_0}^{t_1} \left( \int_{t_0'}^{t'} G(t'') dt'' \right)^2 dt' \qquad (2)$$

which for rectangular gradient pulses evaluates to $$b = (\gamma G \delta)^2 (\Delta - \delta/3), \qquad (3)$$

where $\gamma$ is the magnetogyric ratio, G is the amplitude of the gradients pulses, $\delta$ is the duration of the gradient pulses, and $\Delta$ is the separation between the leading edges of the gradient pulses.

D is related to the mean-square displacement $<Z^2>$ through $$\langle Z^2 \rangle = 2Dt \qquad (4)$$

where t is the time interval over which diffusion is measured.

In the limit of short gradient pulses, where molecular displacements during the pulse is insignificant when compared to the displacements during the time between the pulses and the structural length scales of the system, $<Z^2>$ can be estimated from the signal attenuation induced by the DW block using $$I = I_0 e^{-2\pi^2 q^2 \langle Z^2 \rangle} \qquad (5)$$

where q is the wave vector of the magnetization helix induced by the defocusing gradient pulse. The value of q is given by the area of the defocusing gradient pulse by $$q = \frac{\gamma}{2\pi} \int_0^{t_1/2} G(t') dt', \qquad (6)$$

which equals $$q = \frac{\gamma G \delta}{2\pi} \qquad (7)$$

for rectangular gradient pulses.

For systems with Gaussian diffusion, Eq. 5 is still valid if the estimated $<Z^2>$ refers to the displacement occurring during an effective diffusion time $t_d$ given by $$t_d = \Delta - \delta/3 \qquad (8)$$

for rectangular gradient pulses. Even for systems with non-Gaussian diffusion, $<Z^2>$ can be estimated from the initial, low-q, attenuation of the signal under the condition of short gradient pulses as defined above. For the case of gradient pulses with finite length, one can define an apparent mean square displacement $<Z(\delta,\Delta)^2>$ and corresponding apparent diffusion coefficient $D(\delta, \Delta)$ from the initial, low-G, decay of $E=III_0$:

$$\langle Z(\delta, \Delta)^2 \rangle = -\frac{2}{\gamma^2 \delta^2} \lim_{G \to 0} \frac{\partial \ln E(G, \delta, \Delta)}{\partial G^2} \quad (9)$$

and $$D(\delta, \Delta) = \frac{\langle Z(\delta, \Delta)^2 \rangle}{2(\Delta - \delta/3)}. \quad (10)$$

Diffusion in a Spherical Cell

For a fluid with bulk diffusion coefficient $D_0$ confined in a spherical cavity with radius r, $\langle Z(\delta,\Delta)^2 \rangle$ can according to WO2008/147326 be shown to be $$\langle Z(\delta, \Delta)^2 \rangle = \quad (11)$$

$$4 \sum_{m=1}^{\infty} \frac{1}{\alpha_m^2(\alpha_m^2 r^2 - 2)} \times \frac{2\alpha_m^2 D\delta - 2 + 2e^{-\alpha_m^2 D_0 \delta} + 2e^{-\alpha_m^2 D_0 \Delta} - e^{-\alpha_m^2 D_0 (\Delta-\delta)} - e^{-\alpha_m^2 D_0 (\Delta+\delta)}}{(\alpha_m^2 D_0 \delta)^2}$$

where $\alpha_m$ are the roots of $$\alpha_m r J'_{3/2}(\alpha_m r) - \frac{1}{2} J_{3/2}(\alpha_m r) = 0. \quad (12)$$

By making a series expansion of the exponentials in Eq. (11), the following limiting behaviours are obtained:

$$\langle Z(\delta = 0, \Delta)^2 \rangle = 4 \sum_{m=1}^{\infty} \frac{1 - e^{-\alpha_m^2 D_0 \Delta}}{\alpha_m^2(\alpha_m^2 r^2 - 2)}. \quad (13)$$

$$\langle Z(\delta, \Delta = \infty)^2 \rangle = 8 \sum_{m=1}^{\infty} \frac{1}{\alpha_m^2(\alpha_m^2 r^2 - 2)} \times \frac{\alpha_m^2 D_0 \delta - 1 + e^{-\alpha_m^2 D_0 \delta}}{(\alpha_m^2 D_0 \delta)^2}. \quad (14)$$

$$\langle Z(\delta = 0, \Delta \ll r^2/D_0)^2 \rangle = 2 D_0 \Delta \quad (15)$$

$$\langle Z(\delta = 0, \Delta = \infty)^2 \rangle = \frac{2}{5} r^2. \quad (16)$$

$$\langle Z(\delta \gg r^2/D_0, \Delta = \infty)^2 \rangle = \frac{8 r^4}{D_0 \delta} \sum_{m=1}^{\infty} \frac{1}{\alpha_m^4 r^4(\alpha_m^2 r^2 - 2)} \approx \frac{0.183 r^4}{D_0 \delta}. \quad (17)$$

The restricted and non-restricted cases coincide at short $t_d$. For the restricted case, an upper limit is reached at long $t_d$ and short $\delta$. When the DW block is used as a filter, to remove the signal from non-restricted components, $\delta$ and $\Delta$ should chosen to maximize the difference of $\langle Z(\delta,\Delta)^2 \rangle^{1/2}$ between the free and restricted components, while keeping $\delta$ and $\Delta$ much shorter than the characteristic time for exchange between the components. The equations above make a rational design of DW filters possible.

Molecular Exchange Between Extra- and Intracellular Components

The ratio between the number of molecules in the intra- and extracellular compartments, $n_i$ and $n_e$, is the equilibrium constant K:

$$K = \frac{n_e}{n_i}. \quad (18)$$

Self-diffusion in the intra- and extracellular fluids occur with the diffusion coefficients $D_{i,0}$ and $D_e$. For convenience, the effects of obstruction of the extracellular fluid originating from the presence of the spherical cells are included in $D_e$. The effective diffusion coefficient $D_i$ of the intracellular fraction depends on the values of $\delta$ and $\Delta$ according to Eqs. (10) and (11). Molecular exchange takes place across the cell membrane with permeability P. The outward and inward exchange rates $k_i$ and $k_e$ are given by $$k_i = 3P/r \quad (19)$$

and $$k_e = \frac{k_i}{K}. \quad (20)$$

The exchange rates are related to the mean residence times in the intra- and extracellular phases, $\tau_i$ and $\tau_e$, via $$\tau_i = 1/k_i$$

$$\tau_e = 1/k_e \quad (21)$$

Using a macroscopic approach, the signal attenuation during the DW block can be calculated by solving the differential equation $$\frac{dM_i}{dt} = -4\pi^2 q^2 D_i - k_i M_i + k_e M_e \quad (22)$$

$$\frac{dM_e}{dt} = -4\pi^2 q^2 D_e + k_i M_i - k_e M_e.$$

for the magnetizations in the intra- and extracellular phases, $M_i$ and $M_e$, using the initial condition $$M_{i,0} = \frac{M_0}{1+K} \quad (23)$$

$$M_{e,0} = \frac{M_0}{1+K^{-1}}$$

where $M_0$ is the total magnetization at equilibrium. Eq. (22) assumes Gaussian diffusion in the two phases with the diffusion coefficients $D_i$ and $D_e$. Exchange between the two phases occurs with the rate constants $k_i$ and $k_e$. In Eq. (22), there is no reference to the microscopic geometry of the system. Within the short gradient pulse approximation, the solution to Eq. (22) for the intra- and extracellular magnetizations $M_{i,1}$ and $M_{e,1}$, at the time $t_1$ is $$M_{i,1} = \frac{1}{2}\left(M_{i,0} - \frac{BM_{i,0} - k_e M_{e,0}}{C}\right)e^{-(A-C)\Delta} + \quad (24)$$

$$\frac{1}{2}\left(M_{i,0} + \frac{BM_{i,0} - k_e M_{e,0}}{C}\right)e^{-(A+C)\Delta}$$

$$M_{e,1} = \frac{1}{2}\left(M_{e,0} + \frac{BM_{e,0} + k_i M_{i,0}}{C}\right)e^{-(A-C)\Delta} +$$

$$\frac{1}{2}\left(M_{e,0} - \frac{BM_{e,0} + k_i M_{i,0}}{C}\right)e^{-(A+C)\Delta}$$

where $$A = 2\pi^2 q^2 (D_i + D_e) + \frac{k_i + k_e}{2} \quad (25)$$

$$B = 2\pi^2 q^2 (D_i - D_e) + \frac{k_i + k_e}{2}$$

$$C = \sqrt{B^2 + k_i k_e}$$

The total NMR signal is proportional to the sum of $M_i$ and $M_e$ and the ratio $III_0$ equals $(M_{i,1}+M_{e,1})/(M_{i,0}+M_{e,0})$.

The following modifications of Eq. (24) are performed to make it valid also for exchange between a spherical cell and a continuous medium and having gradient pulses of finite length: $D_i$ is calculated with Eqs. (10) and (11) and $\Delta$ in the exponentials are replaced with $t_d$. This modification is expected to be accurate as long as $\delta \ll \tau_i, \tau_e$. The derived expression may e.g. accurately describe the diffusion weighting for water in a packed sediment of yeast cells over a wide range of values of $\delta$ and $\Delta$. Fitting Eq. (24) to experimental data yields estimates of the time scale for exchange, but this approach is not practical for clinical application since the dependence of the experimentally observed signal intensities on the exchange time is rather weak.

DW Filter: Removing the Extracellular Signal

Using the model disclosed above and reasonable assumptions about the values of $D_{i,0}$, $D_e$, r, K, and P, it is possible make a judicious choice of a $\{\delta,\Delta,G\}$ parameter set designed to remove the signal originating from the extracellular component while keeping the signal from the intracellular one. More efficiently, an iterative numerical procedure can be used to find the set $\{\delta,\Delta,G\}$ that minimizes the signal from the extracellular component for a given attenuation of the intracellular one.

Numerical methods can be used according to WO2008/147326 to solve Eq. (22) when the condition $\delta \ll \tau_i, \tau_e$ is not fulfilled or if the gradient modulation is more complicated than a rectangular one.

Diffusion-Diffusion Exchange

Figure 2:
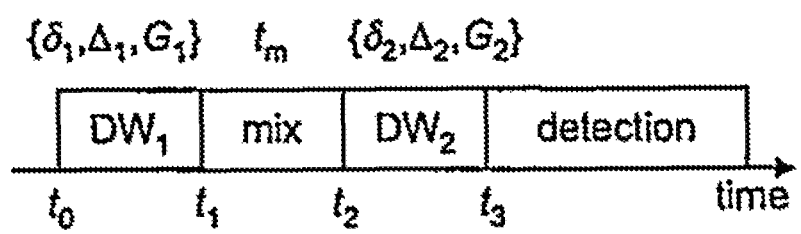
FIG. 2 shows a schematic picture of a pulse sequence to encode NMR or MRI for molecular exchange between components with fast and slow diffusion.

A schematic picture of the pulse sequence to encode NMR or MRI for molecular exchange between components with fast and slow diffusion is displayed in FIG. 2. Two diffusion weighting blocks, $DW_1$ and $DW_2$, separated by a mixing block with duration $t_m$ precede signal detection. Each DW block in FIG. 2 obey the same constraints and can be analyzed in a similar way as the DW block in FIG. 1. The time points $t_0$, $t_1$, $t_2$, and $t_3$ are indicated in the figure. For each of these time points $t_n$, one can estimate the amplitudes of the intracellular, extracellular, and total magnetizations $M_{i,n}$, $M_{e,n}$ and $M_n = M_{i,n} + M_{e,n}$, respectively. The change of the magnetizations during the time period between $t_0$ and $t_1$ is given by Eq. (24).

Neglecting nuclear relaxation processes, the effect of the mixing block is to redistribute the magnetization between the intra- and extracellular components, while preserving the overall magnitude of the total magnetization, i.e. $M_2 = M_1$. The relative contributions to the total magnetization after the mixing time can be shown to be $$\frac{M_{i,2}}{M_2} = \frac{M_{i,0}}{M_0} - \left(\frac{M_{i,0}}{M_0} - \frac{M_{i,1}}{M_1}\right) e^{-(k_i+k_e)t_m} \quad (26)$$

$$\frac{M_{e,2}}{M_2} = \frac{M_{e,0}}{M_0} - \left(\frac{M_{e,0}}{M_0} - \frac{M_{e,1}}{M_1}\right) e^{-(k_i+k_e)t_m}.$$

The evolution of the magnetizations $M_i$ and $M_e$ during the $DW_2$ block, the time period between $t_2$ and $t_3$, is again given by Eq. (24). Thus, $M_{i,3}$ and $M_{e,3}$ can be calculated by application of Eq. (24), then Eq. (26), and finally Eq. (24) again. The theoretical expression for the signal after the $DW_1$-mix-$DW_2$ sequence may be essential for a rational design of new protocols.

Generalization

The analysis above has for simplicity been focused on exchange between two components: one freely diffusing and one confined in a spherical cavity with a permeable membrane. Those skilled in the art will realize that the analysis above, and the protocols to be presented below, can be generalized to relaxation instead of diffusion, and other geometries, number of components, and gradient modulation schemes.

Callaghan's Protocols

The same general pulse sequence as the one shown in FIG. 2 was previously introduced by Callaghan (Callaghan, Furó. J. Chem. Phys. 2004, 120, 4032). The method according to Callaghan is performed in the following way:

1) Keep $\delta_1 = \delta_2$, $\Delta_1 = \Delta_2$, and $t_m$ constant, vary $G_1$ and $G_2$ independently (typically in 16×16=256 separate steps), and perform a 2D inverse Laplace transform. The presence of "cross peaks" in the thus obtained diffusion-diffusion exchange 2D correlation spectrum indicates exchange on the timescale of the $t_m$.

2) Repeat the protocol described in 1) for a series of $t_m$ (typically 4 or 8, thus yielding 16×16×8=2048 separate steps). A numerical estimate of $(k_i + k_e)$ is obtained by analysis of the variation of the volume of the cross peaks as a function of $t_m$.

New Protocols According to WO2008/147326 in Comparison with Callaghan

The protocols according to WO2008/147326 differ from the ones introduced by Callaghan in the way the parameters describing each DW block are varied and the way of analyzing the data, thereby leading to orders of magnitude shorter experiment time for the same information content. This reduction in experiment time is crucial for the practical implementation in a clinical setting. In WO2008/147326 the following protocols are suggested:

1) Find a set of $\{\delta_1, \Delta_1, G_1\}$ to reduce the extracellular component as much as possible without affecting the intracellular one (e.g. by an educated guess or a numerical procedure). Find a set of $\{\delta_2, \Delta_2, G_2\}$ to completely reduce the extracellular component while retaining as much as possible of the intracellular one. Choose a reasonable mixing time $t_m$ based on the expected exchange rate and the nuclear relaxation times. Record image 1 using the parameters $\{\delta_1, \Delta_1, G_1, t_m, \delta_2, \Delta_2, G_2\}$ and image 2 with $\{\delta_1, \Delta_1, G_1=0, t_m, \delta_2, \Delta_2, G_2\}$. The difference image obtained by subtracting image 1 from image 2 yields signal intensity only if there is molecular exchange on the time scale defined by the experimental variables. This protocol gives the same information as Callaghan 1) above at more than 100 times shorter experiment time.

2) Repeat the protocol described in 1) for a series of $t_m$. A numerical estimate of $k_i + k_e$ is obtained by analysis of the variation of the signal intensity as a function of $t_m$. Once again, this protocol gives the same information as Callaghan 2) above at more than 100 times shorter experiment time.

3) Repeat a protocol with $\{\delta_1, \Delta_1, G_1, t_m, \delta_2, \Delta_2, G_2\}$ for a series of $G_2$ and $t_m$ (typically 16×7=116 separate steps). Complement with a series of $G_2$ at the smallest value of $t_m$ and using $G_1=0$ (typically 16 steps). This latter series improves the accuracy of the estimated parameters according to WO2008/147326. Analysis according to the following section yields estimates of $k_i$, $k_e$, and K.

Data Evaluation

While the data evaluation required for protocols 1) and 2) are trivial—taking the difference between two images and exponential fitting to a series of difference images, respectively—the evaluation of protocol 3) is somewhat less straightforward. The more advanced analysis is more than well justified by estimating parameters that are directly related to the cellular microstructure and dynamics, instead of the more phenomenological parameters of the new protocols 1) and 2) and Callaghan's protocols.

E.g. for water in a yeast cell sediment there is a clear difference between a slow (intracellular) and fast (extracellular) component in a plot of NMR signal vs. b, defined in Eq. (2), when the $DW_1$ block is turned off ($G_1=0$). This data series is equivalent to what would be obtained with infinitely long $t_m$. Such a measurement is impossible to perform in practice since the signal would be reduced below the noise level because of nuclear relaxation processes. The fast component disappears when turning the $DW_I$ block on ($G_1=0.30$ $Tm^{-1}$). Increasing $t_m$ leads to the reappearance of the fast component on expense of the slow one. This observation is an unambiguous indication of molecular exchange between the intra- and extracellular components.

For data fitting purposes it is according to WO2008/147326 convenient to rewrite Eqs. (24) to (26) as $$I_n(b) = I_{0,n}(X_{i,n}e^{-bD_i} + X_{e,n}e^{-bD_e}) \quad (27)$$

where $$X_{i,n} = X_{i,0} - (X_{i,0} - X_{i,1})e^{-kt_{m,n}} \quad (28)$$

and $$X_{e,n} = 1 - X_{i,n}. \quad (29)$$

In Eqs. (27)-(29) above and all Eqs. below, the observables and variables $I_n(b)$, $X_{i,n}$, $X_{e,n}$, $P_n(D)$ $\langle D_n \rangle$, $t_{m,n}$ for data series with different $t_m$ are labeled with the index n. As justified above, the series n=0 with $G_1=0$ is treated as a series with $t_m=\infty$. The data series labeled with n=1 refers to $t_m=0$. In Eq. (27), b refers to the $DW_2$ block. Replacing Eq. (24) with a biexponential as in Eq. (27) is an approximation which is expected to be good as long as $\tau_i$ and $\tau_e$ are much longer than $\delta$ and $\Delta$ in each DW block. Eq. (27) with Eqs. (28) and (29) are fitted to the entire set of experimental data using $D_i$, $D_e$, k, $X_{i,0}$, $X_{i,1}$ and the set of $I_{0,n}$ as adjustable parameters. The system parameters K and $k_i$, are related to the fit parameters k and $X_{i,0}$ through $$K = \frac{1 - X_{i,0}}{X_{i,0}} \quad (30)$$

and $$k_i = \frac{k}{1 + K^{-1}}. \quad (31)$$

A global fit according to WO2008/147326, as described above, yields the most accurate results of the estimated parameters.

For systems that are more complicated than yeast cell sediments, the biexponential function in Eq. (27) can be replaced with other multiexponential expressions. Alternatively, one can relate the signal $I_n(b)$ to a diffusion coefficient distribution $P_n(D)$ through $$I_n(b) = \int_0^\infty P_n(D)e^{-bD}\,dD. \quad (32)$$

$P_n(D)$ can be estimated from the experimental $I_n(b)$ using an inverse Laplace transform (ILT) algorithm. The variation of the amplitudes of the various components in the obtained $P_n(D)$ as a function of $t_m$ can be analyzed for exchange using equations analogous to Eq. (28). Unfortunately ILT algorithms are notorious for their instability, leading to sometimes wildly fluctuating positions of the peaks in $P_n(D)$. According to WO2008/147326, this problem was solved by a customized ILT algorithm where the peak positions (but not the amplitudes) were enforced to be constant for all series with different $t_m$. Imposing the constraint of fixed peak positions for all $P_n(D)$ improves the accuracy of the estimated parameters. For each $P_n(D)$, $X_{i,n}$ is evaluated by integrating the areas of the peaks corresponding to the intra- and extracellular components. In a subsequent step, k, $X_{i,0}$, and $X_{i,1}$ are estimated by fitting Eq. (28) to the data. The estimated parameters agree favourably with the results of the previously described global fitting procedure. The ILT method of analysis is more general than the global fitting, but in order to improve the numerical stability more data points and consequently longer experiment time is required.

Description of Specific Embodiments According to the Present Invention

As may be noticed from the summary of the invention above, the method according to the present invention is directed to encoding, detecting and acquiring the magnetic resonance signal from said object by limitation to initial decay of the signal intensity I. According to the present invention this may be accomplished by use of different types of weighting blocks before and after the mixing block (i.e. the first and second weighting block). Therefore, according to one specific embodiment of the present invention there is provided a method according to the invention, wherein the first weighting block is a first relaxation weighting block with relaxation weighting $\tau_1$ and the second weighting block is a second relaxation block with relaxation weighting $\tau_2$, and wherein encoding, detecting and acquiring the magnetic resonance signal from said object is limited to the initial decay of the signal intensity I with increasing $\tau_1$ or $\tau_2$, to obtain the apparent relaxation rate R;

or wherein the first weighting block is a first diffusion weighting block with diffusion weighting $b_1$ and the second weighting block is a second diffusion block with diffusion weighting $b_2$, and wherein encoding, detecting and acquiring the magnetic resonance signal from said object is limited to the initial decay of the signal intensity I with increasing $b_1$ or $b_2$, to obtain the apparent diffusion coefficient ADC;

and wherein the variation of the apparent relaxation rate R or the apparent diffusion coefficient ADC with $t_m$ thereafter is analysed to obtain the apparent exchange rate AXR.

In the case of relaxation weighting blocks according to the present invention, these may be defined by the relaxation weighting variables $\tau_1$ and $\tau_2$ instead of $b_1$ or $b_2$ as in the case of diffusion weighting blocks. The relaxation rate R may refer to any of the commonly known nuclear relaxation rates $R_1$ (longitudinal or spin-lattice), $R_2$ (transverse or spin-spin), or $R_{1\rho}$ (spin-lattice in the rotating frame)

According to the present invention, the obtained apparent exchange rate AXR may be used for generating image contrast. It is important to realize that not only the main parameter AXR, but also σ (sigma) explained below, ADC, and the set of $I_{0,n}$ by themselves or in combination could be used to generate a greyscale or color image. As an example, AXR may give red level, ADC green and sigma blue.

Due to the limited gradient strength on clinical MRI scanners it is difficult to acquire data for sufficiently high values of b to allow for a global two-component fit or ILT analysis as described above. Another problem with clinical MRI is the in general high noise levels. When working with diffusion weighting blocks according to the present invention, one could in such a case limit the analysis to initial slope of $I_n(b)$, according to $$\lim_{b \to 0} I_n(b) = I_{0,n}e^{-b\langle D_n\rangle} \quad (33)$$

where the effective decay rate is given by $\langle D_n \rangle$, the average value of $P_n(D)$:

$$\langle D_n \rangle = \frac{\int_0^\infty D P_n(D) dD}{\int_0^\infty P_n(D) dD}. \quad (34)$$

For two-site exchange $\langle D_n \rangle$ is approaching the equilibrium value $\langle D_0 \rangle$ exponentially according to $$\langle D_n \rangle = \langle D_0 \rangle - (\langle D_0 \rangle - \langle D_1 \rangle) e^{-k t_{m,n}} \quad (35)$$

The expression in Eq. (35) follows from Eq. (28).

Therefore, according to one specific embodiment of the present invention, when using diffusion weighting blocks, the first weighting block is a first diffusion weighting block with diffusion weighting $b_1$ and the second weighting block is a second diffusion block with diffusion weighting $b_2$, and wherein limitation of encoding, detecting and acquiring the magnetic resonance signal is made according to the following:

$$\lim_{b \to 0} I_n(b) = I_{0,n} e^{-b \langle D_n \rangle} \quad (36)$$

where the variable b refers to either $b_1$ or $b_2$ and $\langle D_n \rangle$ is the apparent diffusion coefficient.

Moreover, according to yet another specific embodiment of the present invention, the self-diffusion coefficient $\langle D_n \rangle$ is given by the average value of the diffusion coefficient distribution $P_n(D)$ according to the following:

$$\langle D_n \rangle = \frac{\int_0^\infty D P_n(D) dD}{\int_0^\infty P_n(D) dD}. \quad (37)$$

According to yet another embodiment of the present invention, the variation of $\langle D_n \rangle$ with $t_{m,n}$ depends on the exchange rate k according to the following:

$$\langle D_n \rangle = \langle D_0 \rangle - (\langle D_0 \rangle - \langle D_1 \rangle) e^{-k t_{m,n}} \quad (38)$$

in which $\langle D_0 \rangle$ is $\langle D_n \rangle$ at equilibrium and $\langle D_1 \rangle$ is $\langle D_n \rangle$ at $t_{m,n} = 0$.

Even for multi-site exchange, Eq. (36) with Eq. (38) is a good approximation to the evolution of the NMR signal with $t_m$. In analogy with the concept of the apparent diffusion coefficient (ADC) being used in conventional DW MRI, the value of k should in the multi-site case be considered as an apparent exchange rate (AXR) which has the potential to become a valuable mode of contrast in MRI. For the analysis of experimental data Eq. (33) with Eq. (35) is rewritten as $$I_n(b) = I_{0,n} \exp\{-ADC \cdot [1 - \sigma \exp(-AXR \cdot t_{m,n})] \cdot b\} \quad (39)$$

where $ADC = \langle D_0 \rangle$ and $$\sigma = \frac{\langle D_0 \rangle - \langle D_1 \rangle}{\langle D_0 \rangle}. \quad (40)$$

is limited to the range $0 < \sigma < 1$. Large values of σ are obtained for broad P(D) and efficient DW filters.

In line with the disclosure above, according to one specific embodiment of the present invention, the encoding, detecting and acquiring is made for multi-site exchange. According to another specific embodiment, the apparent exchange rate (AXR) for multi-site exchange is calculated according to the following:

$$I_n(b) = I_{0,n} \exp\{-ADC \cdot [1 - \sigma \exp(-AXR \cdot t_{m,n})] \cdot b\} \quad (41)$$

where $ADC = \langle D_0 \rangle$ and $$\sigma = \frac{\langle D_0 \rangle - \langle D_1 \rangle}{\langle D_0 \rangle}. \quad (42)$$

wherein σ is limited in the range of $0 < \sigma < 1$.

The present invention may be used for different objects, such as e.g. a zeolite, a liposome, vesicle or a biological cell.

Moreover, when using diffusion weighting blocks, the parameters defining these blocks may be organised in different configurations. According to one specific embodiment of the present invention, the first weighting block is a first diffusion weighting block with diffusion weighting $b_1$ and the second weighting block is a second diffusion block with diffusion weighting $b_2$ and wherein one of the following is valid:

- $b_1$ is in on or off mode, $b_2$ is fixed and $t_m$ is fixed;
- $b_2$ is in on or off mode, $b_1$ is fixed and $t_m$ is fixed;
- $b_1$ is in on or off mode, $b_2$ is fixed and $t_m$ is varied;
- $b_2$ is in on or off mode, $b_1$ is fixed and $t_m$ is varied;
- $b_1$ is fixed, $b_2$ is varied and $t_m$ is varied, which is complemented by a series where $b_1$ equals zero, $t_m$ is fixed and $b_2$ is varied; or
- $b_2$ is fixed, $b_1$ is varied and $t_m$ is varied, which is complemented by a series where $b_2$ equals zero, $t_m$ is fixed and $b_1$ is varied.

By the term "in on or off mode" is herein meant that a parameter in on or off mode may in such a case only have two values, either zero, i.e. off, or something else, i.e. on. In the case of $b_1$ being in on or off mode, $b_2$ and $t_m$ being fixed it is according to present invention possible to achieve a difference image and thereby information regarding if there is an exchange or not just by doing a series of trials according to (2×1×1), i.e. two trials.

As another example, in the case of $b_1$ being in on or off mode, $b_2$ being fixed and $t_m$ being varied it is according to present invention possible to achieve a series of difference images and thereby the exchange rate $(k_i + k_e)$.

As yet another example, in the case of $b_1$ being fixed, $b_2$ being varied and $t_m$ being varied, and then a complemented series where $b_1$ equals zero, $t_m$ is fixed and $b_2$ is varied it is according to the present invention possible to achieve the exchange rate $k_i$ from a global bimodal fit giving the exchange rate $(k_i + k_e)$ and fraction $X_{i,0}$.

According to another specific embodiment of the present invention, a method is provided wherein an asymmetric pulse pair or gradient modulation is used to increase the filter efficiency. The time integral of the effective gradient modulation should however evaluate to zero at the end of the diffusion weighting block.

According to one specific embodiment of the present invention a numerical optimization is made to increase the filter efficiency.

According to yet another embodiment of the present invention there is provided a system for magnetic resonance imaging or nuclear magnetic resonance spectroscopy comprising a radio frequency and a gradient pulse unit for emitting a radio frequency and gradient pulse sequence towards an object being subjected to a magnetic field, wherein said object comprises a molecule having an atom with a nuclear spin differing from 0;

a detector unit for detecting a magnetic resonance signal from said object corresponding to said emitted radio frequency and gradient pulse sequence; wherein the radio frequency and gradient pulse sequence comprises a first weighting block, a mixing block with duration $t_m$ and a second weighting block; wherein the detector unit is provided for detection which is limited to the initial decay of the signal intensity I with increasing strength of at least one of the first weighting block and the second weighting block, so that the variation of the initial signal decay rate with $t_m$ may be analysed to obtain the apparent exchange rate AXR.

According to another specific embodiment, there is provided a system according to the present invention, wherein the first weighting block is a first relaxation weighting block with relaxation weighting $\tau_1$ and the second weighting block is a second relaxation block with relaxation weighting $\tau_2$, and wherein encoding, detecting and acquiring the magnetic resonance signal from said object is limited to the initial decay of the signal intensity I with increasing $\tau_1$ or $\tau_2$, to obtain the apparent relaxation rate R;

or wherein the first weighting block is a first diffusion weighting block with diffusion weighting $b_1$ and the second weighting block is a second diffusion block with diffusion weighting $b_2$, and wherein encoding, detecting and acquiring the magnetic resonance signal from said object is limited to the initial decay of the signal intensity I with increasing $b_1$ or $b_2$, to obtain the apparent diffusion coefficient ADC;

so that the variation of the apparent relaxation rate R or the apparent diffusion coefficient ADC with $t_m$ thereafter may be analysed to obtain the apparent exchange rate AXR.

Moreover, according to another specific embodiment, the system according to above further comprises an image creation unit configured to create an image based on said magnetic resonance signal.

According to another embodiment, there is provided a medical workstation comprising means for performing the method according to the present invention.

Moreover, according to specific embodiments there is provided the use of the method, system or medical workstation according to the present invention, as a diagnostic tool for diagnosing a disease or disorder, for studying the metabolism of living cells in vivo or for studying the transmembrane diffusion of a medical drug through the cell membranes.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

Detailed Description of the Drawings

FIG. 1 shows a schematic of a pulse sequence to encode an NMR spectrum or MR image for molecular diffusion. The signal intensity is attenuated by a diffusion weighting block, DW, preceding signal detection. The DW block consists of a pair of gradient pulses of duration δ and amplitude G, having the opposite effective polarity. Δ is the time between the onset of the gradient pulses. The time points in the beginning and the end of the DW block are labeled $t_0$ and $t_1$, respectively. The diffusion weighting b is given by Eq. (3).

FIG. 2 shows a schematic of a pulse sequence to encode the NMR spectrum or MR image for molecular exchange between components with slow and fast diffusion. Two diffusion weighting blocks, $DW_1$ and $DW_2$, are separated by a mixing block with duration $t_m$. Each DW block is similar to the expansion shown in FIG. 1. A diffusion weighting b can be calculated for each block using Eq. (3). The evolution of the intra- and extracellular magnetizations $M_i$ and $M_e$ between time points $t_0$-$t_1$, $t_1$-$t_2$, and $t_2$-$t_3$ can be calculated with Eq. (24), (26), and (24), respectively.

Figure 3:
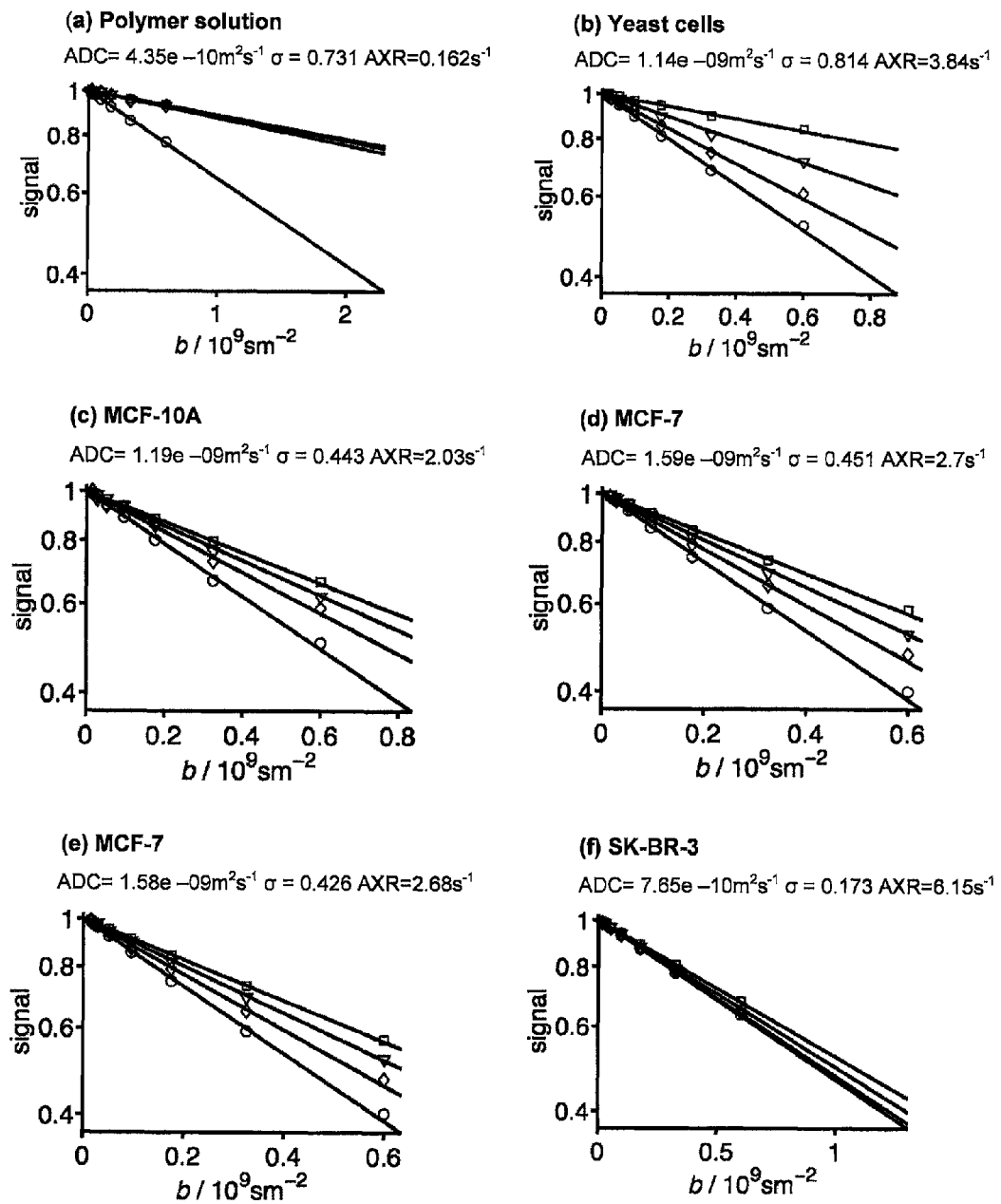
FIG. 3 shows data on experiments performed on different solutions and cells with the method according to the present invention.

FIG. 3 shows data on experiments performed on different solutions and cells with the method according to the present invention. Normalized MR signal intensity vs. the diffusion weighting b of the $DW_2$ diffusion weighting block is shown in all of the graphs a-f. Experimental data is shown as symbols with the following meanings: circles (data series n=0: $DW_1$ diffusion weighting $b_1$=0, $t_m$=29.0 ms which corresponds to $t_m$=∞), squares (data series n=1: $b_1$=2.76·10$^9$ sm$^{-2}$, $t_m$=29.0 ms), triangles (data series n=2: =2.76·10$^9$ sm$^{-2}$, $t_m$=128.0 ms), and diamonds (data series n=3: $b_1$=2.76·10$^9$ sm$^{-2}$, $t_m$=328.0 ms). The lines indicate the result of a global model fit of Eq. (36) yielding estimates of ADC, AXR, and σ. The investigated samples are (a) Aqueous poly(ethylene glycol) solution, (b) Yeast cells, (c) MCF-10A healthy breast cells, (d) and (e) MCF-7 cancerous breast cells with oestrogen receptors, and (f) SK-BR-3 cancerous breast cells without oestrogen receptors.

In comparison to previous protocol described in WO2008/147326, less signal attenuation is needed to get the information about exchange which means that correspondingly lower values of b and G can be used. The protocol can thus be implemented on any clinical MRI scanner. Less signal attenuation also means that the signal is less affected by noise.

The invention claimed is:

1. Method for magnetic resonance imaging or nuclear magnetic resonance spectroscopy comprising emitting a radio frequency and gradient pulse sequence towards an object being subjected to a magnetic field, wherein said object comprises a molecule having an atom with a nuclear spin differing from 0;

encoding, detecting and acquiring a magnetic resonance signal from said object corresponding to said emitted radio frequency and gradient pulse sequence, wherein the radio frequency and gradient pulse sequence comprises a first weighting block, a mixing block with duration $t_m$ and a second weighting block;

wherein encoding, detecting and acquiring the magnetic resonance signal from said, object is limited to initial decay of the signal intensity I with increasing strength of at least one of the first weighting block and the second weighting block, wherein the variation of the initial signal decay rate with $t_m$ is analyzed to obtain the apparent exchange rate AXR.

2. Method according to claim 1, wherein the first weighting block is a first relaxation weighting block with relaxation weighting $\tau_1$ and the second weighting block is a second relaxation block with relaxation weighting $\tau_2$, and wherein encoding, detecting and acquiring the magnetic resonance signal from said object is limited to the initial decay of the signal intensity I with increasing $\tau_1$ or $\tau_2$, to obtain the apparent relaxation rate R;

or wherein the first weighting block is a first diffusion weighting block with diffusion weighting $b_1$ and the second weighting block is a second diffusion block with diffusion weighting $b_2$, and wherein encoding, detecting and acquiring the magnetic resonance signal from said object is limited to the initial decay of the signal intensity I with increasing $b_1$ or $b_2$, to obtain the apparent diffusion coefficient ADC;

and wherein the variation of the apparent relaxation rate R or the apparent diffusion coefficient ADC with $t_m$ thereafter is analysed to obtain the apparent exchange rate AXR.

3. Method according to claim 1, wherein AXR is used for generating image contrast.

4. Method according to claim 1, wherein the first weighting block is a first diffusion weighting block with diffusion weighting $b_1$ and the second weighting block is a second diffusion block with diffusion weighting $b_2$, and wherein limitation of encoding, detecting and acquiring the magnetic resonance signal is made according to the following:

$$\lim_{b \to 0} I_n(b) = I_{0,n} e^{-b \langle D_n \rangle}$$

where the variable b refers to either $b_1$ or $b_2$ and $\langle D_n \rangle$ is the apparent diffusion coefficient.

5. Method according to claim 4, wherein the variation of $\langle D_n \rangle$ with $t_{m,n}$ depends on the exchange rate k according to the following:

$$\langle D_n \rangle = (\langle D_0 \rangle - \langle D_1 \rangle) - \langle D_1 \rangle) e^{-k t_{m,n}}$$

in which $\langle D_0 \rangle$ is $\langle D_n \rangle$ at equilibrium and $\langle D_1 \rangle$ is $\langle D_n \rangle$ at $t_{m,n} = 0$.

6. Method according to claim 1, wherein the encoding, detecting and acquiring is made for multi-site exchange.

7. Method according to claim 6, wherein the apparent exchange rate (AXR) for multi-site exchange is calculated according to the following:

$$I_n(b) = I_{0,n} \exp\{-ADC \cdot [1 - \sigma \exp(-AXR \cdot t_{m,n})] \cdot b\}$$

where $ADC = \langle D_0 \rangle$ and $$\sigma = \frac{\langle D_0 \rangle - \langle D_1 \rangle}{\langle D_0 \rangle}$$

wherein $\sigma$ is limited in the range of $0 < \sigma < 1$.

8. Method according to claim 1, wherein the object is a zeolite, a liposome, vesicle or a biological cell.

9. Method according to claim 1, wherein the first weighting block is a first diffusion weighting block with diffusion weighting $b_1$ and the second weighting block is a second diffusion block with diffusion weighting $b_2$, and wherein one of the following is valid:

$b_1$ is in on or off mode, $b_2$ is fixed and $t_m$ is fixed;
$b_2$ is in on or off mode, $b_1$ is fixed and $t_m$ is fixed;
$b_1$ is in on or off mode, $b_2$ is fixed and $t_m$ is varied;
$b_2$ is in on or off mode, $b_1$ is fixed and $t_m$ is varied;
$b_1$ is fixed, $b_2$ is varied and $t_m$ is varied, which is complemented by a series where $b_1$ equals zero, $t_m$ is fixed and $b_2$ is varied; or
$b_2$ is fixed, $b_1$ is varied and $t_m$ is varied, which is complemented by a series where $b_2$ equals zero, $t_m$ is fixed and $b_1$ is varied.

10. Method according to claim 1, wherein an asymmetric pulse pair or gradient modulation is used to increase the filter efficiency.

11. Method according to claim 1, wherein a numerical optimization is made to increase the filter efficiency.

12. Medical workstation comprising means for performing the method according to claim 1.

13. Use of a method according to claim 1, as a diagnostic tool for diagnosing a disease or disorder.

14. Use of a method according to claim 1, for studying the metabolism of living cells in vivo.

15. Use of a method according to claim 1, for studying the transmembrane diffusion of a medical drug through the cell membranes.

16. System for magnetic resonance imaging or nuclear magnetic resonance spectroscopy comprising a radio frequency and a gradient pulse unit for emitting a radio frequency and gradient pulse sequence towards an object being subjected to a magnetic field, wherein said object comprises a molecule having an atom with a nuclear spin differing from 0;

a detector unit for detecting a magnetic resonance signal from said object corresponding to said emitted radio frequency and gradient pulse sequence;

wherein the radio frequency and gradient pulse sequence comprises a first weighting block, a mixing block with duration $t_m$ and a second weighting block;

wherein the detector unit is provided for detection which is limited to the initial decay of the signal intensity I with increasing strength of at least one of the first weighting block and the second weighting block, so that the variation of the initial signal decay rate with $t_m$ may be analyzed to obtain the apparent exchange rate AXR.

17. System according to claim 16, wherein the first weighting block is a first relaxation weighting block with relaxation weighting $\tau_1$ and the second weighting block is a second relaxation block with relaxation weighting $\tau_2$, and wherein encoding, detecting and acquiring the magnetic resonance signal from said object is limited to the initial decay of the signal intensity I with increasing $\tau_1$ or $\tau_2$, to obtain the apparent relaxation rate R;

or wherein the first weighting block is a first diffusion weighting block with diffusion weighting $b_1$ and the second weighting block is a second diffusion block with diffusion weighting $b_2$, and wherein encoding, detecting and acquiring the magnetic resonance signal from said object is limited to the initial decay of the signal intensity I with increasing $b_1$ or $b_2$, to obtain the apparent diffusion coefficient ADC;

so that the variation of the apparent relaxation rate R or the apparent diffusion coefficient ADC with $t_m$ thereafter may be analysed to obtain the apparent exchange rate AXR.

18. System according to claim 16, further comprising an image creation unit configured to create an image based on said magnetic resonance signal.

* * * * *